US006197981B1

(12) United States Patent
Liu

(10) Patent No.: US 6,197,981 B1
(45) Date of Patent: Mar. 6, 2001

(54) PROCESS FOR CONVERTING 9-DIHYDRO-13-ACETYLBACCATIN III INTO TAXOL AND DERIVATIVES THEREOF

(75) Inventor: Jian Liu, 470 Cherry Avenue, Fredericton, New Brunswick E3A 5N9 (CA)

(73) Assignee: Jian Liu, Fredericton (CA)

( * ) Notice: Subject to any disclaimer, the term of this patent is extended or adjusted under 35 U.S.C. 154(b) by 0 days.

(21) Appl. No.: 09/423,049

(22) PCT Filed: May 1, 1998

(86) PCT No.: PCT/CA98/00401

§ 371 Date: Nov. 1, 1999

§ 102(e) Date: Nov. 1, 1999

(87) PCT Pub. No.: WO98/50378

PCT Pub. Date: Nov. 12, 1998

(30) Foreign Application Priority Data

May 1, 1997 (CA) .................................. 2204197

(51) Int. Cl.[7] .................................. C07D 305/14

(52) U.S. Cl. ............................................ 549/510; 549/511
(58) Field of Search ...................................... 549/510, 511

(56) References Cited

U.S. PATENT DOCUMENTS 5,530,020 * 6/1996 Gunawardana et al. ............. 514/449

OTHER PUBLICATIONS

Nicolaou, K.C., "Total Synthesis of Taxol. 4.", J. Am. Chem. Soc., vol. 117, No. 2, pp. 653–659, 1995.*
Nicolaou et al, "The Conquest of Taxol.," Angewandte Chemie., International Edition, vol. 34, No. 19, pp. 2079–2090, 1995.*

* cited by examiner

Primary Examiner—Ba K. Trinh
(74) Attorney, Agent, or Firm—Paul S. Sharpe; Marks & Clerk

(57) ABSTRACT

Process for preparing taxol, baccatin III and 10-deacetylbaccatin III by oxidation of 9-dihydro-13-acetylbaccatin III.

16 Claims, No Drawings

PROCESS FOR CONVERTING 9-DIHYDRO-13-ACETYLBACCATIN III INTO TAXOL AND DERIVATIVES THEREOF

This application is a 371 of PCT/CA98/00401 dated May 1, 1998.

FIELD OF THE INVENTION

The present invention relates to a process for converting 9-dihydro-13-acetylbaccatin III into taxane, and is particularly concerned with a process for converting 9-dihydro-13-acetylbaccatin III into taxol, baccatin III, 10-deacetylbaccatin III and their intermediates.

BACKGROUND OF THE INVENTION

Paclitaxel (taxol), represented by the following structural formula:

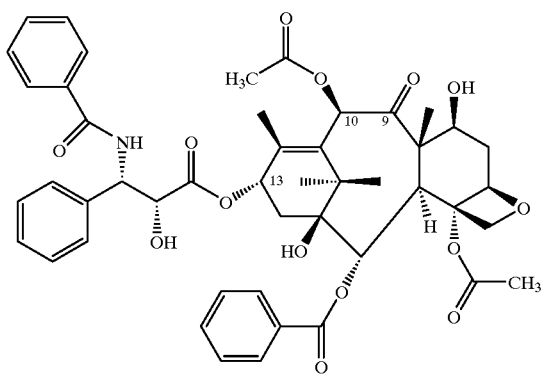

is a potent antitumor compound. Paclitaxel exhibits a unique mechanism for preventing the growth of cancer cells by affecting the microtubules, which play an important role in cell division and other cell functions. At the beginning of cell division, a large number of microtubules are produced, and as the division reaches an end, the microtubules are normally broken down. Taxol prevents microtubules from breaking down, which has the effect of clogging up cancer cells to an extent that the cells cease to grow and divide.

Taxol is clinically effective for the treatment of refractory human ovarian and breast cancer, and has exhibit promising activity against a number of other types of cancers such as liver, peritoneal, cervical, prostate, colon, and esophageal cancers.

Taxol was primarily extracted from the bark of the Pacific yew *Taxus brevifolia*. Unfortunately, the yew grows very slow, approximately eight inches per year, and therefore the tree is a limited source of taxol. This has lead researchers to seek alternative means for producing taxol and analogs thereof which may display superior antitumor activity.

SUMMARY OF THE INVENTION

In one aspect of the present invention, there is provided a process for preparing a taxane comprising the step of oxidizing the C-9 position of 9-dihydro-13-acetylbaccatin III with a suitable oxidizing reagent such as tetra-n-propylammonium perruthenate, Collin's reagent or activated methyl sulfoxide (DMSO).

In another aspect of the present invention, there is provided a process for preparing taxol and a derivative thereof comprising the steps of:

(a) protecting the C-7 hydroxy group of 9-dihydro-13-acetylbaccatin III with a suitable protecting group to obtain a protected product; and (b) oxidizing the C-9 hydroxy group of the protected product. Preferably, the protecting group is selected from the group consisting of benzyl, substituted benzyl, benzylformate, substituted benzylformate, tosyl, substituted tosyl, dihydropyran, methoxymethyl, benzoyl and substituted benzoyl.

The process may further include the steps of deacetylating the C-13 position, and deprotection of the C-7 position to obtain baccatin III. Alternatively, following the C-13 deacetylation, the C-10 position can be deacetylated and the C-7 position can be deprotected to obtain 10-deacetylbaccatin III. Or alternatively, following the C-13 deacetylation, a suitable side chain can be added to the C-13 position and the resulting intermediate selectively deprotected to obtain a desired product such as taxol. To obtain taxol, the deprotection is done at the C-7 and 2' positions. Suitable side chains are (2R, 2S)-N-benzoyl-O-(1-ethoxyethyl)-3-phenylisoserine and (3R, 4S)-3-(1-ethoxyethoxy)-4-(phenyl)-N-benzoyl-2-azetidinone.

In accordance with another aspect of the present invention, there is provided a compound having the following chemical structure:

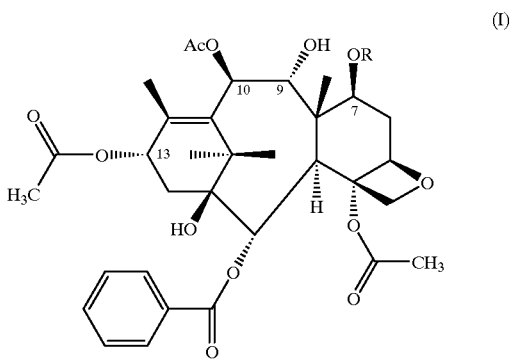

(I)

wherein R is selected from the group consisting of benzyl, substituted benzyl, benzylformate, substituted benzylformate, tosyl, substituted tosyl, dihydropyran, methoxymethyl, benzoyl, substituted benzoyl, benzoylmethyl and substituted benzoylmethyl.

In accordance with another aspect of the present invention, there is provided a compound of the formula:

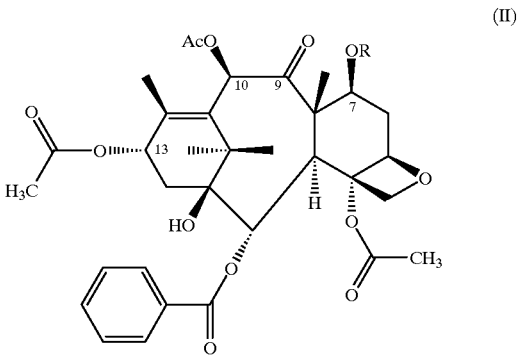

(II)

wherein R is selected from the group consisting of benzyl, substituted benzyl, benzylformate, substituted benzylformate, tosyl, substituted tosyl, dihydropyran, methoxymethyl, benzoyl, substituted benzoyl, benzoylmethyl and substituted benzoylmethyl.

DETAILED DESCRIPTION OF THE INVENTION

Table 1 lists definitions and chemical structures of compounds as used herein, and those definitions and chemical structures are to be applied throughout the present specification.

TABLE 1

Definitions And Chemical Structures

| Name | Definition/chemical structure |
|---|---|
| Functional group | an atom or group of atoms having a characteristic chemical reactivity |
| Benzyl | 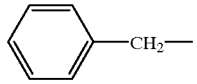 |
| Substituted benzyl | a benzyl group as defined above substituted with one or more functional group(s) |
| Dihydropyran |  |
| Benzylformate | 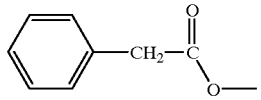 |
| Substituted benzylformate | a benzylformate as defined above substituted with one or more functional group(s) |
| Methoxymethyl | —$CH_2$—O—$CH_3$ |
| Benzoylmethyl | 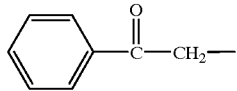 |
| Substituted benzoylmethyl | a benzoylmethyl as defined above substituted with one or more functional group(s) |
| Tosyl | 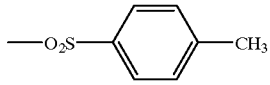 |
| Substituted tosyl | a tosyl as defined above substituted with one or more functional group(s) |

The starting material, 9-dihydro-13-acetylbaccatin III, can be obtained by various means including by extraction of Taxus species as described in Applicant's Canadian Patent Application No. 2,203,844 filed on Apr. 28, 1997 and will be published at the end of October 1998. Briefly, the isolation process entails collecting plant material such as stems and needles, and grounding and extracting the material with methanol. The extraction is carried through for about 24 hours, and the resulting mixture is filtered and the extract collected. The extract is concentrated to about 10% of its original volume by evaporation, and further diluted with water. The aqueous solution is extracted several times with hexane to give an aqueous layer and a non-aqueous layer.

The aqueous layer is extracted several times with chloroform or dichloromethane. The chloroform or dichloromethane extract is concentrated to dryness, and the residue is dissolved in a mixture of chloroform, methanol and acetone (10:1:0.5), and fractionated by dry column chromatography to obtain fractions of taxol and 9-dihydro-13-acetylbaccatin III. The fractions are combined, extracted and the 9-dihydro-13-acetylbaccatin III is crystallized out.

Taxol and derivatives thereof may be synthesized from 9-dihydro-13-acetylbaccatin III by a number of protection, oxidation, reaction and deprotection steps. For example, referring to the processes illustrated below in Schemes 1–3, 9-dihydro-13-acetylbaccatin III is first protected at the C-7 position by adding a protecting group such as a methoxybenzyl or tosyl group to form a protected intermediate such as compound 2, 7 or 16. Other suitable protecting groups are substituted benzyl, dihydropyran, benzylformate (CBZ), substituted benzylformate, methoxymethyl (MOM), benzoylmethyl (BOM) and substituted benzoylmethyl.

The protected intermediate is oxidized at the C-9 position with a suitable oxidizing agent such as tetra-n-propylammonium perruthenate (TPAP), Collin's reagent (chromium trioxide and pyridine in dichloromethane) or activated methyl sulfoxide (DMSO) to give an oxidized intermediate such as compound 3, 8 or 17. The oxidized intermediate may be deacetylated at the C-13 position by reaction with, for example butyllithium in hexane or methyllithium, to give a baccatin III analog such as compound 4 or 9. Depending of the desired product, the baccatin III analog can either be deprotected with, for example 2,3-dichloro-5,6-dicyanobenzoquinone (DDQ) to yield baccatin III (15) or further reacted to eventually obtain 10-deacetylbaccatin III (13) or taxol (18) or other desirable products.

To obtain 10-deacetylbaccatin III, the baccatin III analog (4) is next deacetylated at the C-10 position by reaction with, for example triethylamine in sodium hydride, to compound 12 which is further deprotected. To obtain taxol, the C-13 taxol side chain is added to the baccatin III analog by reaction with, for example, (2R, 2S)-N-benzoyl-O-(1-ethoxyethyl)-3-phenylisoserine and lithium hexamethyldisilazide, to give a taxol analog such as compound 5 or 10. The taxol analog is next deprotected at the 2' by reaction with, for example 1% hydrochloric aced, and C-7 position by reaction with, for example triethylamine and UV light, to give taxol. Other suitable C-13 side chains such as (3R, 4S)-3-(1-ethoxyethoxy)-4-(phenyl)-N-benzoyl-2-azetidinone may also be used to obtain taxol analogs.

It will be appreciated by one skilled in the art that other reagents and reactants may be used to obtain the same results, and that protection, oxidation and deprotection steps may be carried out in varying orders or number of steps, as necessary, and that schemes 1–3 are intended to include such variations.

SCHEME 1
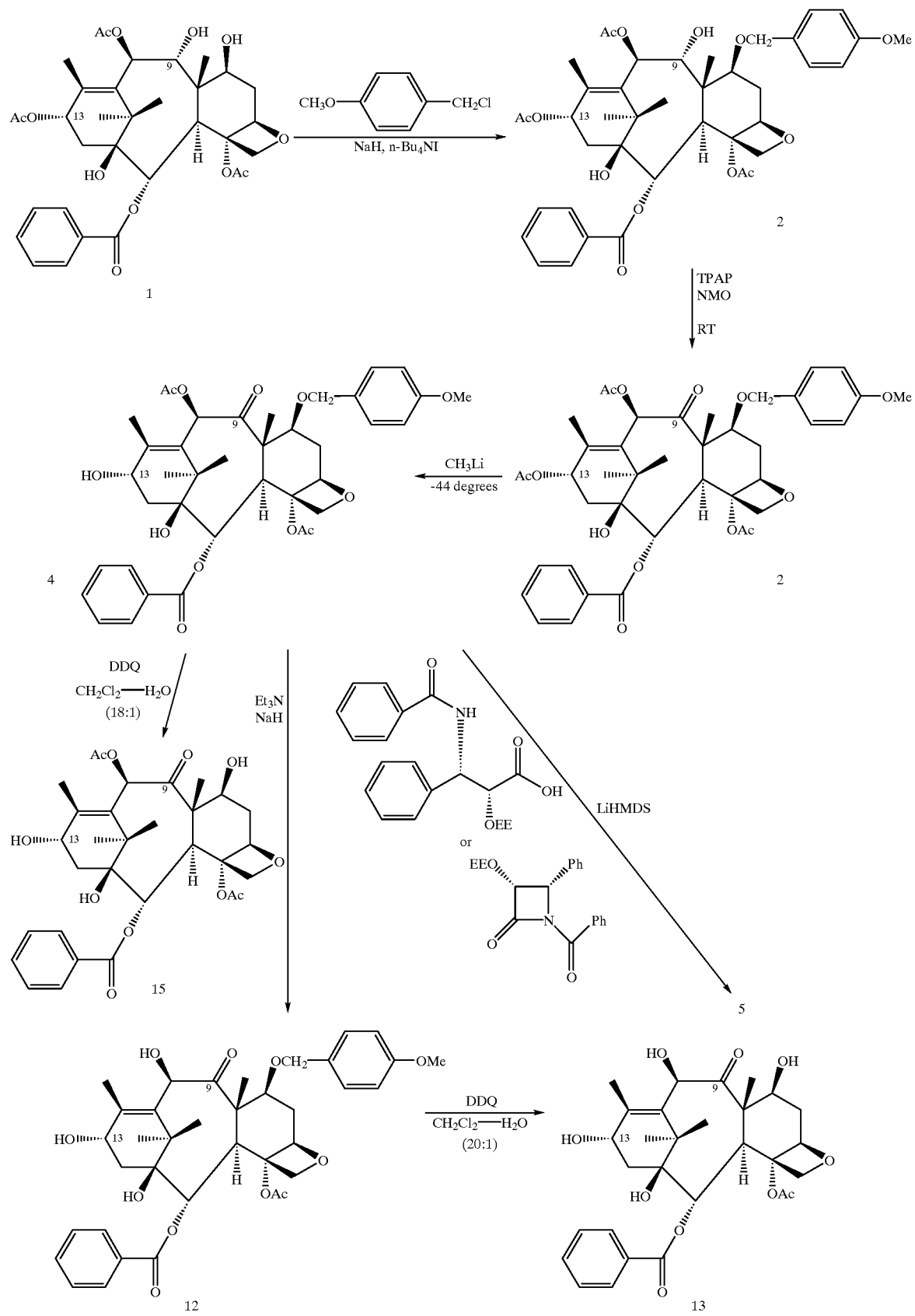

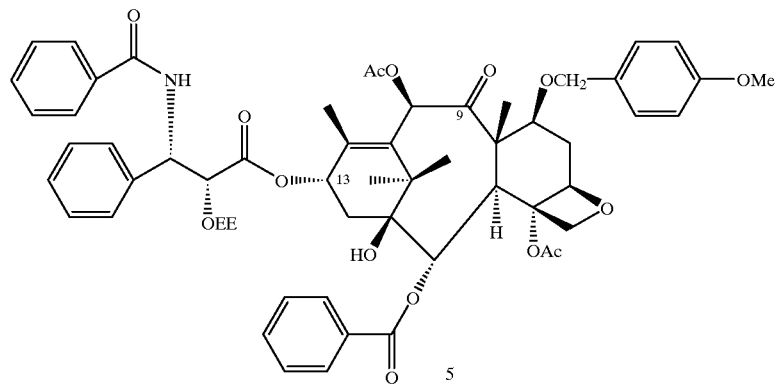
5
↓ 1% HCl
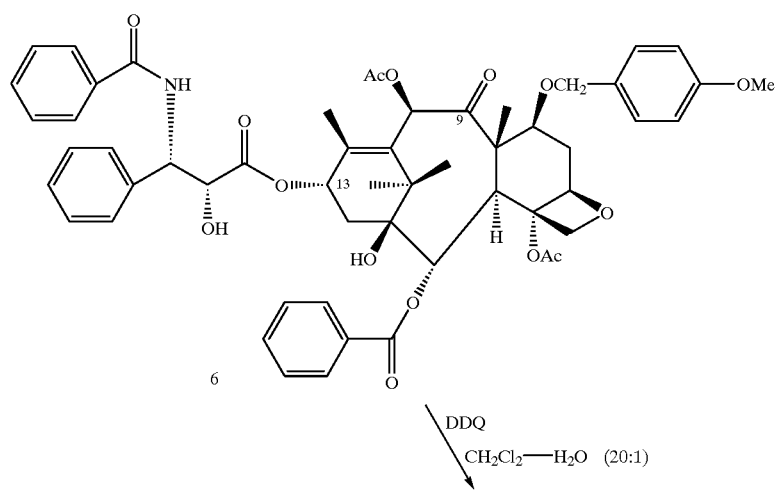
6
↓ DDQ
CH$_2$Cl$_2$—H$_2$O (20:1)
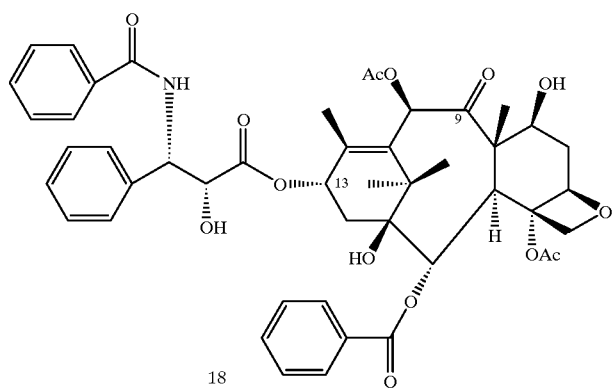
18

SCHEME 2
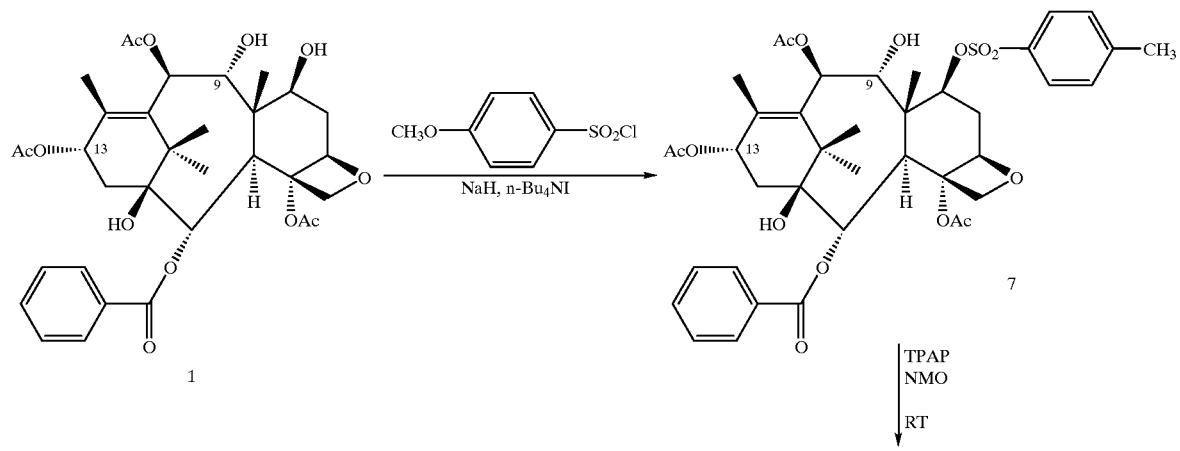
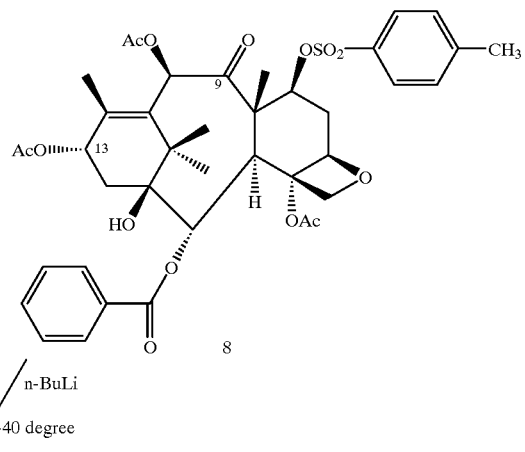
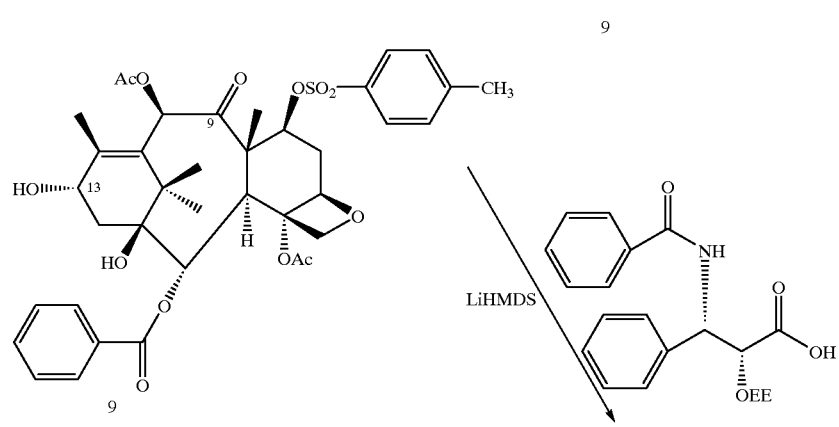

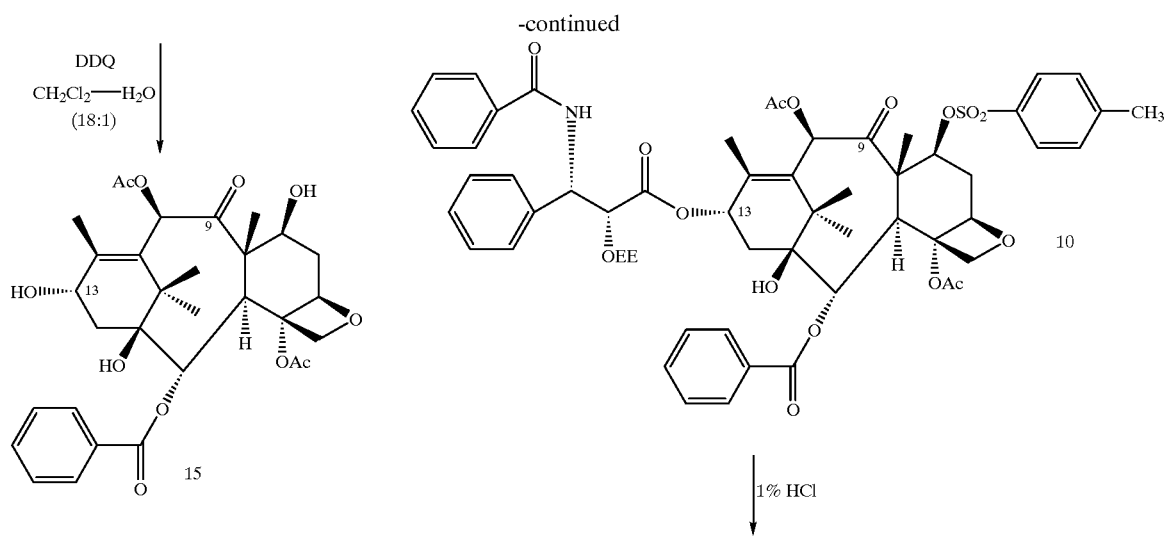
-continued
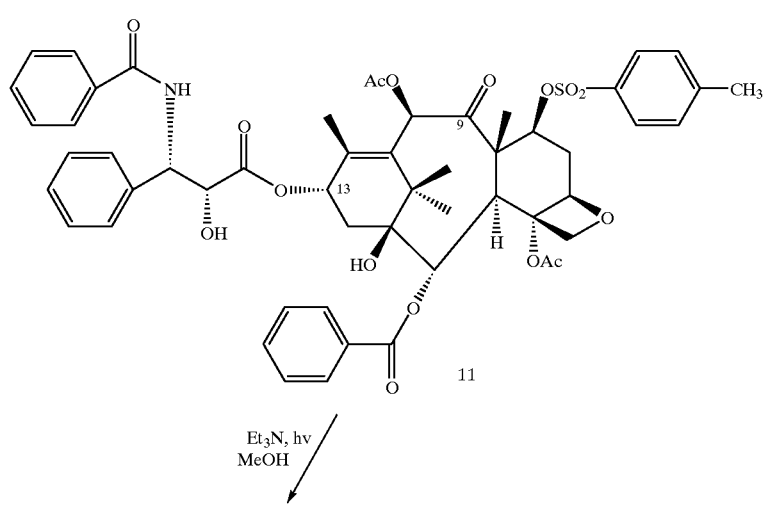
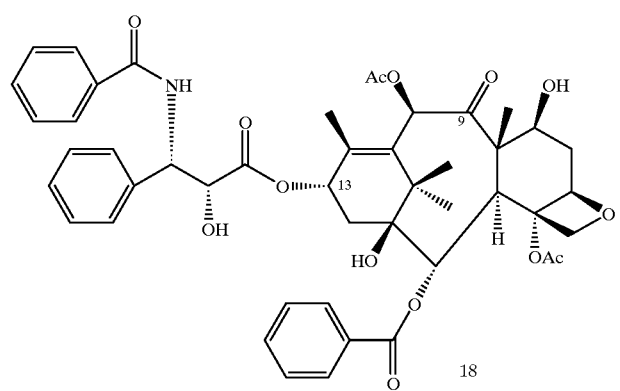

SCHEME 3

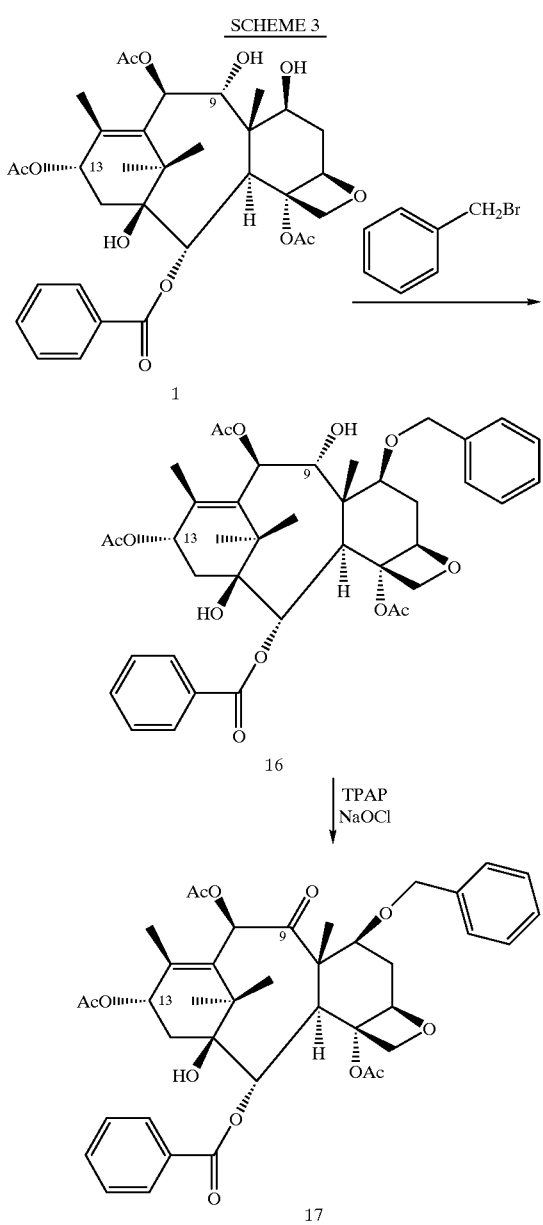

1 9-dihydro-13-acetylbaccatin III
2 7-O-p-methoxybenzyl-9-dihydro-13-acetylbaccatin III
3 7-O-p-methoxybenzyl-13-acetylbaccatin III
4 7-O-p-methoxybenzylbaccatin III
5 7-O-p-methoxybenzyl-(2'-ethoxyethyl) taxol
6 7-O-p-methoxybenzyl taxol
7 7-O-tosyl-9-dihydro-13-acetylbaccatin III
8 7-O-tosyl-13-acetylbaccatin III
9 7-O-tosylbaccatin III
10 7-O-tosyl-(2'-ethoxyethyl) taxol
11 7-O-tosyl taxol
12 10-deacetyl-7-O-p-methoxybenzylbaccatin III or 7-O-p-methoxybenzyl-10-deacetylbaccatin III
13 10-deacetylbaccatin III
15 Baccatin III
16 7-O-benzyl-9-dihydro-13-acetylbaccatin III
17 7-O-benzyl-13-acetylbaccatin III
18 taxol or paclitaxel Material All the reagents are obtained from Aldrich Chemicals, USA.

EXAMPLE 1

Preparation of Taxol

Step 1(a): 7-O-p-methoxybenzyl-9-dihydro-13-acetylbaccatin III (2)

20 mg 9-dihydro-13-acetylbaccatin III (1) and 100 mg n-tetrabutylammonium iodide were dissolved in 3 mL of dichloromethane ($CH_2Cl_2$) in a 25 mL round bottom flask. 23 mg of sodium hydride (NaH) was added and the mixture was stirred at room temperature for five minutes. 0.1 mL of p-methoxybenzyl chloride was added dropwise over 5 minutes, and the temperature was raised to 45° C. The mixture was stirred for 24 hours, following which 30 mL of distilled water was added to stop the reaction. The product was extracted with dichloromethane, and purified by preparative thin layer chromatography (TLC) to yield 17 mg 7-O-p-methoxybenzyl-9-dihydro-13-acetylbaccatin III, compound 2, as identified by NMR spectroscopy.

$^1$H-NMR (200 MHz, $CDCl_3$), δ: 8.10 (d, Ar—H-2, H-6), 7.60 (t, Ar—H-4), 7.50 (t, Ar—H-3, H-5), 7.21 (d, 2Ar—H), 6.90 (d, 2Ar—H), 6.30 (d, H-10), 6.17 (t, H-13), 5.80 (d, H-2), 4.92 (d, H-5), 4.75 (dd, H-7), 4.50 (d, H-9), 4.31 (d, H-20a), 4.29 (d, H-20b), 4.15 (s, —$OCH_2$), 3.80 (s, $OCH_3$), 3.01 (s, H-3), 2.59 (m, H-6), 2.26 (s, $CH_3C$=O), 2.18 (s, $CH_3C$=O), 2.10 (H-14a), 2.02 (s, $CH_3C$=O), 1.97 (s, $CH_3$), 1.85 (H-14b), 1.77 (s, $CH_3$), 1.75 (s, $CH_3$), 1.26 (S, $CH_3$) ppm.

Step 1(b): 7-O-methoxybenzyl-13-acetylbaccatin III (3)

10 mg of the product of step 1(a), compound 2 was added to 10.8 mg of 4-methylmorpholine N-oxide (NMO) in a 25 mL round bottom flask, and the mixture was dissolved in 3 mL dichloromethane. 4 Å molecular sieve was adde d to the mixture which was stirred for 5 minutes. 3.5 mg of tetra-n-propylammonium perruthenate (TPAP) was added, and the mixture was stirred for about 6 hours at room temperature, following which the temperature was raised to 40° C. The mixture was maintained at that temperature overnight until the reaction was completed. Once the reaction was completed, the mixture was poured into a short silica gel column. The column was eluted with 50 mL of chloroform ($CHCl_3$) to give a chloroform fraction which was concentrated to dryness. The residue was purified by preparative TLC to yield 2 mg white needles which were identified as 7-O-methoxybenzyl-13-acetylbaccatin III, compound 3, by NMR spectroscopy.

$^1$H-NMR (400 MHz, $CDCl_3$), δ: 8.10 (d, Ar—H-2, H-6), 7.60 (t, Ar—H-4), 7.49 (t, Ar—H-3, H-5), 7.22 (s, 4Ar—H), 6.28 (s, H-10), 6.18 (t, H-13), 5.65 (d, H-2), 5.60 (dd, H-7), 5.27 (s, —$OCH_3$), 4.95 (d, H-5), 4.33 (d, H-20a), 4.17 (d, H-20b), 3.95 (s, —$OCH_2$), 3.81 (d, H-3), 2.60 (m, H-6), 2.35 (s, $CH_3C$=O), 2.22 (dd, H-14a), 2.20 (s, $CH_3C$=O), 2.15 (s, $CH_3$), 2.05 (s, $CH_3C$=O), 2.01 (H-14b), 1.96 (s, $CH_3$), 1.24 (s, $CH_3$), 1.18 (s, $CH_3$) ppm.

Step 1(c): 7-O-p-methoxybenzylbaccatin III (4)

50 mg of the product of step 1(b), compound 3 was dissolved in 5 mL of tetrahydrofuran at −44° C., and 5 mole equivalent of methyllithium were added dropwise to remove the C-13 acetyl group. Upon completion of the deacetylation reaction, the mixture was partitioned between 50 mL of a mixture of saturated ammonium chloride buffer and dichloromethane (1:1). The organic layer was concentrated and purified by flash column chromatography on silica gel, eluting with a mixture of dichloromethane and methanol (97:3) to yield 22 mg of 7-O-p-methoxybenzylbaccatin III as white solid.

Step 1(d): 7-O-p-methoxybenzyl-(2'-ethoxyethyl) taxol (5)

15 mg of the product of step 1(c) (4) was combined with 6 mole equivalents of (2R, 2S)-N-benzoyl-O-(1-ethoxyethyl)-3-phenylisoserine or 5 mole equivalent of (3R, 4S)-3-(1-ethoxyethoxy)-4-(phenyl)-N-benzoyl-2-azetidinone and 3 mole equivalents of lithium hexamethyldisilazide (LiHMDS) in 5 mL of tetrahydrofuran at −78° C. for about 20 minutes in a 25 mL round bottom flask. The reaction was warmed to 0° C. for about 6 hours, or until the reaction was completed as confirmed by TLC analysis. Once the reaction was completed, the mixture was quenched with 30 mL of a pH 7 buffer and the product was extracted with dichloromethane, dried and purified by flash column chromatography on silica gel, eluting with dichloromethane and methanol (97:3) to yield 16 mg of 7-O-p-methoxybenzyl-(2'-ethoxyethyl) taxol.

Step 1(e): 7-O-p-methoxybenzyl taxol (6)

10 mg of the product of step 1(d) was dissolved in ethanol at room temperature in a 5 mL round bottom flask. An excess of 1% hydrochloric acid was added, and the reaction continued for about 4 hours. The reaction product was poured into a 25 mL separation funnel and 50 mL of a mixture of pH 7 buffer and dichloromethane (1:1) was added. The organic layer was evaporated to dryness to obtain a residue.

Step 1(f): taxol or paclitaxel (18)

5 mL of dichloromethane was added to the residue obtained in step 1(e), and 0.25 mL of water was mixed thereto. In this case, the ratio of water to dichloromethane was 1:20. 1.0–1.5 mole equivalent of 2,3-dichloro-5,6-dicyanobenzoquinone (DDQ) was added to the mixture and the temperature was maintained at room temperature or 5° C. Upon completion, 10 mL of saturated aqueous sodium hydrogen carbonate (NaHCO$_3$) was added to the reaction, and the mixture was extracted with 10 mL of dichloromethane. The extract was washed with 5 mL of saturated aqueous sodium hydrogen carbonate and dried over sodium sulfate (Na$_2$SO$_4$). The solvent was evaporated and the residue was purified on a silica gel column to give 3.5 mg of taxol.

EXAMPLE 2

Preparation of Taxol

Step 2(a): 7-O-tosyl-9-dihydro-13-acetylbaccatin III (7)

1.0 g of 9-dihydro-13-acetylbaccatin III (1) was placed in a 50 mL round bottom flask with 454 mg of p-toluenesulfonyl chloride and 589 mg of tetrabutylammonium iodide. The mixture was dissolved in 15 mL of dichloromethane and stirred at room temperature for 5 minutes. 57 mg of sodium hydride was added slowly to the mixture, and the mixture was stirred at room temperature for 2 hours, following which 100 mL of water was added. The mixture was extracted with 70 mL of dichloromethane. The organic layer was concentrated to dryness, and the residue was purified by flash column chromatography on silica gel, eluting with a mixture of dichloromethane and methanol (97:3) to yield 1.1 g of 7-O-tosyl-9-dihydro-13-acetylbaccatin III.

Step 2(b): 7-O-tosyl-13-acetylbaccatin III (8)

400 mg of the product of step 2(a), compound 7, was placed in a 50 mL round bottom flask and 126 mg of 4-methylmorpholine N-oxide was added to thereto. The mixture was dissolved in 5 mL of acetonitrile (CH$_3$CN) and 126 mg of 4 Å molecular sieve was added. The mixture was stirred at room temperature for about 10 minutes, following which 18 mg of TPAP was added. The mixture was stirred for 5 hours at room temperature and poured through a short silica gel column, eluting with dichloromethane. The fraction was further purified by flash column chromatography on silica gel, eluting with a mixture of ethyl acetoacetate (EtOAc) and hexane (7:3) to yield about 350 mg of white crystals which were identified as 7-O-tosyl-13-acetylbaccatin III, purity 98%.

$^1$H-NMR (400 MHz, CDCl$_3$), δ: 8.05 (dd, 2H, Ar—H), 7.74 (d, 2H, tosyl), 7.60 (ddd, Ar—H$_4$), 7.47 (dd, 2H, Ar—H), 7.30 (d, 2H, tosyl), 6.69 (s, H$_{10}$), 6.16 (t, H$_{13}$), 5.66 (dd, H$_2$), 5.30 (dd, H$_7$), 4.85 (dd, H-5), 4.30 (d, H-20a), 4.10 (d, H-20b), 3.00 (s, 3H, tosyl), 3.92 (d, H-3), 2.60 (m, H-6a), 2.42 (s, —OCH$_3$), 2.33 (s, —OCH$_3$), 2.30 (dd, H-14a), 2.21 (s, —OCH$_3$), 2.13 (s, CH$_3$), 2.10 (dd, H-14b), 1.77 (s, CH$_3$), 1.20 (s, CH$_3$), 1.17 (s, CH$_3$) ppm.

Step 2(c): 7-O-tosylbaccatin III (9)

100 mg of the product of step 2(b) (compound 8) was dissolved in 10 mL of tetrahydrofuran in a 25 mL round bottom flask. The flask was then placed into a container which was maintained at −43° C. The solution was stirred and 0.4 mL of n-butyllithium in hexane was added dropwise for about 3 minutes. The mixture was stirred for about 30 minutes with the temperature raised to about 0° C., and was further transferred into a 500 mL separation funnel with 100 mL of water and extracted with 150 mL of dichloromethane. The product was purified by preparative TLC to yield about 62 mg of white crystals which were identified as 7-O-tosylbaccatin III.

Step 2(d): 7-O-tosyl-(2'-ethoxyethyl) taxol (10)

100 mg of compound 8 was placed in a 25 mL round bottom flask, and 6 mole equivalents of (2R, 2S)-N-benzoyl-O-(1-ethoxyethyl)-3-phenylisoserine were dissolved in 5 mL of tetrahydrofuran at −78° C. 3 mole equivalents of LiHMDS was added slowly. The mixture was stirred at −78° C. for about 20 minutes, following which it was warmed to about 0 to 20° C. The reaction progress was followed by TLC until completion. Once completed, the reaction was quenched with pH 7 buffer and extracted with 40 mL of dichloromethane. The organic layer was concentrated to dryness under vacuum, and the residue was purified by preparative TLC to yield about 85 mg of white crystals which were identified as 7-O-tosyl-(2'-ethoxyethyl) taxol.

Step 2(e): 7-O-tosyl taxol (11)

50 mg of the product of step 2(d), compound 10, was placed in a 25 mL round bottom flask and dissolved with 15 mL of ethanol at room temperature. An excess of 1% hydrochloric acid was added and the mixture was maintained at room temperature for about 5 hours. The reaction was then quenched with 20 mL of water and 40 mL of dichloromethane. The organic layer was evaporated to dryness under vacuum to yield 7-O-tosyl taxol.

Step 2(f): taxol or paclitaxel (18)

The residue obtained in step 2(e) was dissolved in 10 mL of a 0.02 M solution of triethylamine in methanol and irradiated by UV light for about 6 hours or until the reaction is completed as shown by TLC. After irradiation, the triethylamine solvent was evaporated under vacuum. The residue was purified by flash column chromatography on silica gel, eluting with a mixture of dichloromethane and methanol (97:3) to yield about 25 mg of taxol which was characterized as natural taxol.

$^1$H-NMR (400 MHz, CDCl$_3$), δ: 8.12, 7.73, 7.61, 7.51, 7.41, 7.38, 6.97, 6.27, 6.23, 5.78, 5.67, 4.94, 4.79, 4.40, 4.30, 4.19, 3.79, 3.54, 2.51, 2.46, 2.38, 2.36, 2.28, 2.24, 1.89, 1.89, 1.79, 1.68, 1.24, 1.14 ppm.

EXAMPLE 3

Preparation of 10-deacetylbaccatin III

Step 3(a): 7-O-p-methoxybenzyl-10-deacetylbaccatin III (12)

70 mg of the product of step 1(c), compound 4 was placed in a 25 mL round bottom flask with 5 ml of dichloromethane. 1.5 mole equivalent of sodium hydride was added followed by 3 mL of triethylamine, and the mixture was magnetically stirred for 2 to 3 hours. The reaction progress was monitored by TLC. When the deacetylation was completed, the solution was poured into 25 mL of water and extracted with 30 mL dichloromethane. The organic layer was concentrated to dryness under vacuum. The residue was purified by flash column chromatography to yield 42 mg of 7-O-p-methoxybenzyl-10-deacetylbaccatin III as white solid.

Step 3(b): 10-deacetylbaccatin III (13)

30 mg of compound 12, i.e. 7-O-p-methoxybenzyl-10-deacetylbaccatin III, was placed into a 25 mL round bottom flask with 5 mL of dichloromethane which contained a small amount of water, the ratio of water to dichloromethane being 1:20. 1.0 mole equivalent of 2,3-dichloro-5,6-dicyanobenzoquinone (DDQ) was added and the mixture was stirred at room temperature for about 3 hours. Once the reaction was completed, 15 mL of staturated sodium hydrogen carbonate was added and the mixture was extracted with 20 mL of dichloromethane. The extract was dried over sodium sulfate. The dichloromethane solution was evaporated and the residue was purified with a silica gel column to yield 16 mg of 10-deacetylbaccatin III.

EXAMPLE 4

Preparation of Baccatin III 25 mg of compound 4 (7-O-p-methoxybenzylbaccatin III) or 9 (7-O-tosylbaccatin III) containing a small amount of water was placed in a 25 mL round bottom flask and 5 mL of dichloromethane was added. In this case, the ratio of water to dichloromethane was 1:18. 1.0 to 1.5 mole equivalent of DDQ was added to the mixture which was being stirred at about room temperature or 5° C. Upon completion of the reaction, 20 mL of saturated aqueous sodium hydrogen carbonate was added, and the mixture was extracted with 30 mL dichloromethane, and dried over sodium sulfate. The solvent was evaporated and the residue was purified by flash column chromatography, eluting with a mixture of dichloromethane and methanol (96:4) to yield 17 mg of baccatin III, compound 15, as white solid.

EXAMPLE 5

Preparation of 7-O-benzyl-13-acetylbaccatin III intermediate

Step 4(a): 7-O-benzyl-9-dihydro-13-acetylbaccatin III (16)

10 mg of 9-dihydro-13-acetylbaccatin III, compound 1, was dissolved in 3 mL of tetrahydrofuran (THF), and 20 mg of n-tetrabutylammonium iodide was added in a 5 mL round bottom flask. The mixture was stirred for 5 minutes and 12 mg of sodium hydride was added. 170 mg of benzyl bromide was added dropwise and the mixture was stirred at 40° C. The stirring continued overnight. 40 mL of distilled water was added to stop the reaction. The product was extracted with chloroform. The chloroform solution was evaporated and the residue was purified by preparative TLC to yield 8 mg of 7-O-benzyl-9-dihydro-13-acetylbaccatin III.

Step 4(b): 7-O-benzyl-13-acetylbaccatin III (17)

In a similar manner as in step 1(b), compound 17 can be made. In this case, the reagent methylmorphine N-oxide (NMO) is replaced by sodium chloroxide (NaOCl).

Taxol, 10-deacetylbaccatin III and baccatin III can be obtained from 7-O-benzyl-13-acetylbaccatin III in similar manners as shown in the previous examples.

The embodiments of the invention in which an exclusive property or privilege is claimed are defined as follows:

1. A process for converting 9-dihydro-13-acetylbaccatin III into a taxane comprising the step of oxidizing the C-9 position of the 9-dihydro-13-acetylbaccatin III.

2. A process as in claim 1, wherein the oxidizing step is achieve by the addition of an oxidizing agent selected from the group consisting of tetra-n-propylammonium perruthenate, Collin's reagent and activated methyl sulfoxide.

3. A process for preparing taxol and a derivative thereof comprising the steps of:

(a) protecting the C-7 hydroxy group of 9-dihydro-13-acetylbaccatin III with a suitable protecting group to obtain a protected product; and (b) oxidizing the C-9 hydroxy group of the protected product.

4. A process as in claim 3, wherein the protecting group is selected from the group consisting of benzyl, substituted benzyl, benzylformate, substituted benzylformate, tosyl, substituted tosyl, dihydropyran, methoxymethyl, benzoyl and substituted benzoyl.

5. A process as in claim 3, wherein the oxidizing step is achieved by the addition of an oxidizing reagent selected from the group consisting of tetra-n-propylammonium perruthenate, Collin's reagent and activated methyl sulfoxide.

6. A process as in claim 3, further comprising the step of deacetylating the C-13 position.

7. A process as in claim 6, further comprising the step of deprotecting the C-7 position to obtain baccatin III.

8. A process as in claim 6, further comprising the step of deacetylating the C-10 position.

9. A process as in claim 8, further comprising the step of deprotecting the C-7 position to obtain 10-deacetylbaccatin III.

10. A process as in claim 6, further comprising the steps of adding a suitable side chain to the C-13 position and selectively deprotecting to obtain a desired product.

11. A process as in claim 10, wherein the deprotection is done at the C-7 and 2' positions to obtain taxol.

12. A process as in claim 10, wherein the side chain is selected from the group consisting of (2R, 2S)-N-benzoyl-O-(1-ethoxyethyl)-3-phenylisoserine and (3R, 4S)-3-(1-ethoxyethoxy)-4-(phenyl)-N-benzoyl-2-azetidinone.

13. A compound having type formula:

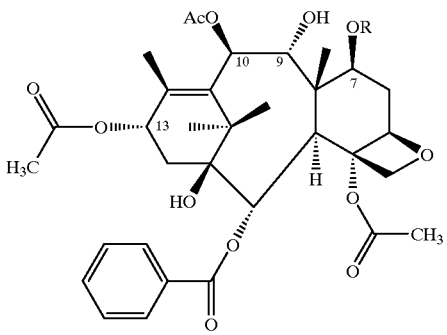

wherein R is selected from the group consisting of benzyl, substituted benzyl, tosyl, substituted tosyl, dihydropyran, methoxymethyl, benzoyl and substituted benzoyl.

14. A compound as in claim 13, wherein the benzyl is benzylformate and the benzoyl is benzoylmethyl.

15. A compound having the formula:

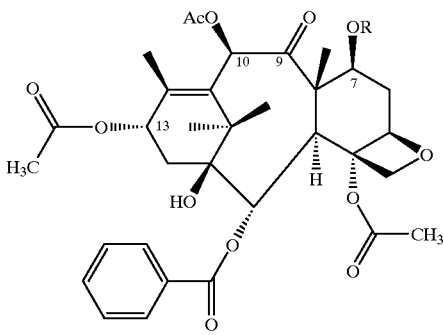

wherein R is selected from the group consisting of benzyl, substituted benzyl, tosyl, substituted tosyl, dihydropyran, methoxymethyl, benzoyl and substituted benzoyl.

16. A compound as in claim 15, wherein the benzyl is benzylformate and the benzoyl is benzoylmethyl.

* * * * *